United States Patent
Chhajlani

(10) Patent No.: US 11,187,697 B2
(45) Date of Patent: Nov. 30, 2021

(54) SUBSTRATE CLEARANCE ASSAYS FOR LYSOSOMAL ENZYMES

(71) Applicant: Takeda Pharmaceutical Company Limited, Osaka (JP)

(72) Inventor: Vijay Chhajlani, Lexington, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 323 days.

(21) Appl. No.: 15/119,324

(22) PCT Filed: Feb. 18, 2015

(86) PCT No.: PCT/US2015/016394
§ 371 (c)(1),
(2) Date: Aug. 16, 2016

(87) PCT Pub. No.: WO2015/126953
PCT Pub. Date: Aug. 27, 2015

(65) Prior Publication Data
US 2017/0219566 A1 Aug. 3, 2017

Related U.S. Application Data

(60) Provisional application No. 61/941,365, filed on Feb. 18, 2014.

(51) Int. Cl.
*G01N 33/50* (2006.01)
*C12N 9/16* (2006.01)
*C12Q 1/44* (2006.01)
*G01N 33/68* (2006.01)
*G01N 33/60* (2006.01)

(52) U.S. Cl.
CPC ........... *G01N 33/5038* (2013.01); *C12N 9/16* (2013.01); *C12Q 1/44* (2013.01); *C12Y 301/06* (2013.01); *C12Y 301/06013* (2013.01); *G01N 33/60* (2013.01); *G01N 33/6893* (2013.01); *G01N 2333/916* (2013.01); *G01N 2500/10* (2013.01); *G01N 2800/7066* (2013.01)

(58) Field of Classification Search
CPC ...... C12N 9/00; C12N 9/2462; C12N 9/2465; C12N 9/16; G01N 33/5038
See application file for complete search history.

(56) References Cited

U.S. PATENT DOCUMENTS

| | | | | |
|---|---|---|---|---|
| 5,989,854 A | * | 11/1999 | Cook | .................... B01L 3/5085 422/71 |
| 8,128,925 B2 | | 3/2012 | Vellard et al. | |
| 8,759,019 B2 | | 6/2014 | Hofer et al. | |
| 2009/0186011 A1 | * | 7/2009 | Vellard | .................... C12N 9/16 424/94.6 |

FOREIGN PATENT DOCUMENTS

| | | |
|---|---|---|
| WO | 0218539 A2 | 3/2002 |
| WO | 2005059163 A2 | 6/2005 |
| WO | 2009/091994 A9 | 7/2009 |
| WO | 2011100392 A2 | 8/2011 |

OTHER PUBLICATIONS

Alouani, "Scintillation Proximity Binding Assay", Methods in Molecular Biology, vol. 138, Chemokine Protocols, Humana Press, p. 135-141, 2000 (Year: 2000).*
https://www.perkinelmer.com/lab-products-and-services/application-supportknowledgebase/radiometric/scintillation-proximity.html, "Scintillation Proximity Assays", 2020 (Year: 2020).*
International Report on Patentability for International Patent Application No. PCT/US2015/016394, dated Aug. 23, 2016 (7 pages).
International Search Report and Written Opinion for International Patent Application No. PCT/US2015/016394, dated Aug. 27, 2015 (9 pages).

* cited by examiner

*Primary Examiner* — Ruth A Davis
(74) *Attorney, Agent, or Firm* — Proskauer Rose LLP; Fangli Chen; Nicholas C. Prairie

(57) ABSTRACT

The present invention provides, among other things, improved substrate clearance assays for lysosomal enzyme that are particularly useful for measuring potency of lysosomal enzymes or other therapeutics for treatment of lysosomal storage diseases. In particular, the present invention combines a physiologically relevant substrate cell assay and an efficient scintillation based detection method.

11 Claims, 12 Drawing Sheets

SUBSTRATE CLEARANCE ASSAYS FOR LYSOSOMAL ENZYMES

RELATED APPLICATIONS

This application is a 35 U.S.C. 371 national stage filing of International Application No. PCT/US2015/016394, filed Feb. 18, 2015, which claims priority to and the benefit of U.S. Provisional Patent Application Ser. No. 61/941,365, filed Feb. 18, 2014, which is hereby incorporated by reference in its entirety.

BACKGROUND

Lysosomal Storage Disorders (LSDs) are rare metabolic disorders associated with lysosomal dysfunction that usually result from deficiency of a lysosomal enzyme required for the metabolism of its substrate such as lipids, or glycoproteins also known as mucopolysaccharides. Among them, mucopolysaccharidoses (MPSs) are a family of LSDs stemming from an inherited deficiency of one of the lysosomal enzymes responsible for degradation of glycosamino glycans (GAGs). GAGs are linear and variably sulfated oligosaccharide chains that are key components of the extracellular matrix and are also involved in cellular signaling in a wide range of processes. A pathogenic accumulation of GAGs in the lysosome, ultimately leads to impairment of cellular function and a wide range of symptoms.

Enzyme replacement therapy (ERT) is an important means for the treatment of LSDs. Typically, ERT involves systemic administration of a natural or recombinantly-derived lysosomal enzyme to subjects in whom the lysosomal enzyme is deficient. Successful ERT requires a potent lysosomal enzyme that can efficiently clear pathogenic accumulation of substrates and restore impaired cellular function.

SUMMARY

The present invention provides an accurate, reliable, simple and highly efficient substrate clearance assay platform to, among other things, assess potency of lysosomal enzymes for enzyme replacement therapy, and any other types of therapeutics (e.g., biologics (e.g., proteins, enzymes, antibodies), small molecules, nucleic acids) for treatment of lysosomal storage diseases. In part, the present invention is based on the unconventional combination of physiological substrate cell assays for lysosomal enzymes and scintillation technology. For example, the present invention has demonstrated that cells, particularly those that lack a relevant endogenous lysosomal enzyme, can synthesize a radiolabeled physiological substrate (e.g., GAGs) by, e.g., growing the cells at a desired cell density (e.g., about 80-98% confluent) in the presence of a radioactive isotope to be incorporated into the substrate (e.g., $^{35}S$). Such cells can be successfully attached to a scintillant base. The radiolabeled substrate inside the cells is close enough to the scintillant base to emit electrons that cause scintillation events. A lysosomal enzyme of interest can then be added to the cells. If the enzyme is potent (i.e., properly internalized, delivered to lysosomes and enzymatically active), the cells are able to metabolize accumulated substrates, resulting in degradation and release of radiolabels from the cells, which can be washed away. Accordingly, reduced signal (i.e., scintillation events) associated with the cells is indicative of the potency of the lysosomal enzyme. As described herein including the Examples section, this method is surprisingly accurate, reproducible and efficient in measuring and quantifying the potency (e.g., relative potency) of a lysosomal enzyme of interest. For example, linearity of a bioassay is an important parameter to measure an assay's ability to obtain accurate test results that are directly proportional to biological potency over a given range. As shown in the Examples, this platform assay has demonstrated an unexpectedly wide linearity range (e.g., at least 40-250%) with high accuracy.

Prior to the present invention, clearance of accumulated GAGs as an effect of exposure to the missing enzyme typically required trypsinization of the cells, several centrifugation and wash steps, lysis of the harvested cells and re-suspension of the lysates in individual tubes of scintillation fluid. As a result, 1 sample usually requires 16 hours of hands-on time. By contrast, the present invention cleverly used the scintillation technology to simplify the process. For example, the present invention does not involve trypsinization, lysis, centrifugation or re-suspension steps. Because decay of free radiolabel in the grow medium is too distant to the scintillant base to produce signal, a clearance assay according to the present invention typically also does not involve extensive wash steps. Furthermore, the present assay platform can use multi-well scintillation plates, for example, those 96-well scintillation plates which typically require only 16 minutes per plate read time on a beta counter. Thus, this assay platform affords significantly increased throughput along with a significantly reduced number of operation steps and hands-on time. The present invention therefore provides a simple and reliable quality control tool for sample characterization during manufacturing and process development. It also provides an analytical tool that can be used to standardize the potency of a lysosomal enzyme or other therapeutic for product approval, labeling and/or packaging. The assay platform described herein may also be used to assess enzyme potency in a biological sample directly obtained from patients for diagnosis and therapy monitoring purposes.

In one aspect, the present invention provides a substrate clearance assay, comprising steps of contacting a sample comprising a lysosomal enzyme of interest with cells containing a substrate of the lysosomal enzyme labeled with a radioactive isotope cleavable (or degradable) by the lysosomal enzyme, under conditions that allow the lysosomal enzyme to cleave, degrade or remove the radioactive isotope from the substrate, wherein the cells are attached to a scintillant base such that scintillation events are indicative of radioactive emission level associated with the cells; and measuring radioactive emission level associated with the cells by detecting scintillation events, wherein a reduction of the radioactive emission level as compared to a baseline radioactive emission level before the contacting step is indicative of clearance of the substrate by the lysosomal enzyme of interest.

In another aspect, the present invention provides a method of measuring potency of a lysosomal enzyme, comprising steps of contacting a sample comprising a lysosomal enzyme of interest with cells containing a substrate of the lysosomal enzyme labeled with a radioactive isotope cleavable (or degradable) by the lysosomal enzyme, under conditions that allow the lysosomal enzyme to cleave, degrade, or remove the radioactive isotope from the substrate, wherein the cells are attached to a scintillant base such that scintillation events are indicative of radioactive emission level associated with the cells; measuring a change of radioactive emission level associated with the cells by detecting scintillation events as compared to baseline scintillation events before the contacting step; and determining the potency of the lysosomal enzyme based on the change of radioactive emission level associated with the cells as compared to a control.

In some embodiments, the cells lack endogenous lysosomal enzyme of interest. In some embodiments, the cells are fibroblasts derived from patients suffering from a lysosomal storage disease associated with the deficiency of the lysosomal enzyme of interest. In some embodiments the substrate of the lysosomal enzyme labeled with the radioactive isotope is synthesized by the cells in the presence of the radioactive isotope.

In some embodiments, the method of measuring potency of a lysosomal enzyme further comprises steps of: growing cells to a desired confluent; treating the cells with the radioactive isotope such that the radioactive isotope is incorporated into newly synthesized substrate of the lysosomal enzyme; and seeding the cells into a well with the scintillant base such that the cells attach to the scintillant base. In some embodiments, the substrate is glycosamine glycan (GAG). In some embodiments, the radioactive isotope is $^{35}S$. In some embodiments, the substrate is labeled by treating the cells with $^{35}S$-sodium sulfate. In some embodiments, the conditions that allow the lysosomal enzyme to cleave the radioactive isotope from the substrate comprises incubating the cells and the sample comprising the lysosomal enzyme at 37° C. with 5% $CO_2$ in atmosphere. In some embodiments, the method of measuring potency of a lysosomal enzyme further comprises a step of washing the cells prior to the measuring step. In some embodiments, the scintillation events are detected by a beta counter.

In some embodiments, the control is a reference standard indicative of a predetermined potency of the lysosomal enzyme of interest and/or a dose-response curve. In some embodiments, the step of determining the potency of the lysosomal enzyme comprises calculating a relative potency using a restricted model. In some embodiments, the step of determining the potency of the lysosomal enzyme is quantitative. In some embodiments, the method of measuring potency of a lysosomal enzyme further comprises a step of determining the total amount of the lysosomal enzyme of interest in the sample. In some embodiments, the method further comprises determining specific activity of the lysosomal enzyme of interest.

In some embodiments, the method of measuring potency of a lysosomal enzyme does not involve trypsinization of the cells. In some embodiments, the method does not involve lysis of the cells.

In some embodiments, the method of measuring potency of a lysosomal enzyme comprises a contacting step that is carried out in the presence of mannose-6-phosphate (M6P) and the method further comprises a step of comparing the clearance or potency to a control measured without M6P to determine if the cellular uptake is M6P dependent.

In some embodiments, the method of measuring potency of a lysosomal enzyme is performed in a high throughput format, in which a plurality of samples are measured simultaneously. In some embodiments, the method comprises the use of a multi-well plate and the base of each individual well is the scintillant base. In some embodiments, the multi-well plate is a 6, 12, 24, 48, or 96-well plate. In some embodiments, the lysosomal enzyme is a sulfatase. In some embodiments, the sulfatase is selected from the group consisting of iduronic acid-2-sulfatase, α-iduronidase, heparan N-sulfatase, acetyl-CoA N-acetyltransferase, α-N-acetylglucosaminidase, β-glucuronidase, N-acetylglucosamine-6-sulfatase, and combination thereof. In some embodiments, the sulfatase is iduronic acid-2-sulfatase. In some embodiments, the sulfatase is heparin N-sulfatase.

In some embodiments, the method of measuring potency of a lysosomal enzyme comprises the sample being a cell culture sample containing the lysosomal enzyme of interest produced recombinantly. In some embodiments, the sample is an eluate or a pooled eluates obtained from a purification process containing purified or partially purified lysosomal enzyme of interest. In some embodiments, the sample is a formulated drug product containing the lysosomal enzyme of interest. In some embodiments, the sample is a tissue sample obtained from a patient. In some embodiments, the tissue sample is a blood sample, a CSF sample, a urine sample, and/or a biopsy sample from a solid organ.

In one aspect, the present invention provides a process for manufacturing the lysosomal enzyme of interest comprising a step of determining the potency of the lysosomal enzyme according to the method described herein. In some embodiments, the step of determining the potency of the lysosomal enzyme is performed before releasing a lot. In some embodiments, the process further comprises a step of adjusting a manufacturing condition based on the potency of the lysosomal enzyme determined.

In some embodiments, the process for purifying the lysosomal enzyme of interest comprises a step of determining the potency of the lysosomal enzyme according to a method of measuring potency of a lysosomal enzyme. In some embodiments, the step of determining the potency of the lysosomal enzyme is performed before releasing a purified lot. In some embodiments, the process further comprises a step of adjusting a purification condition based on the potency of the lysosomal enzyme determined.

As used herein, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

DETAILED DESCRIPTION

Figure 1:
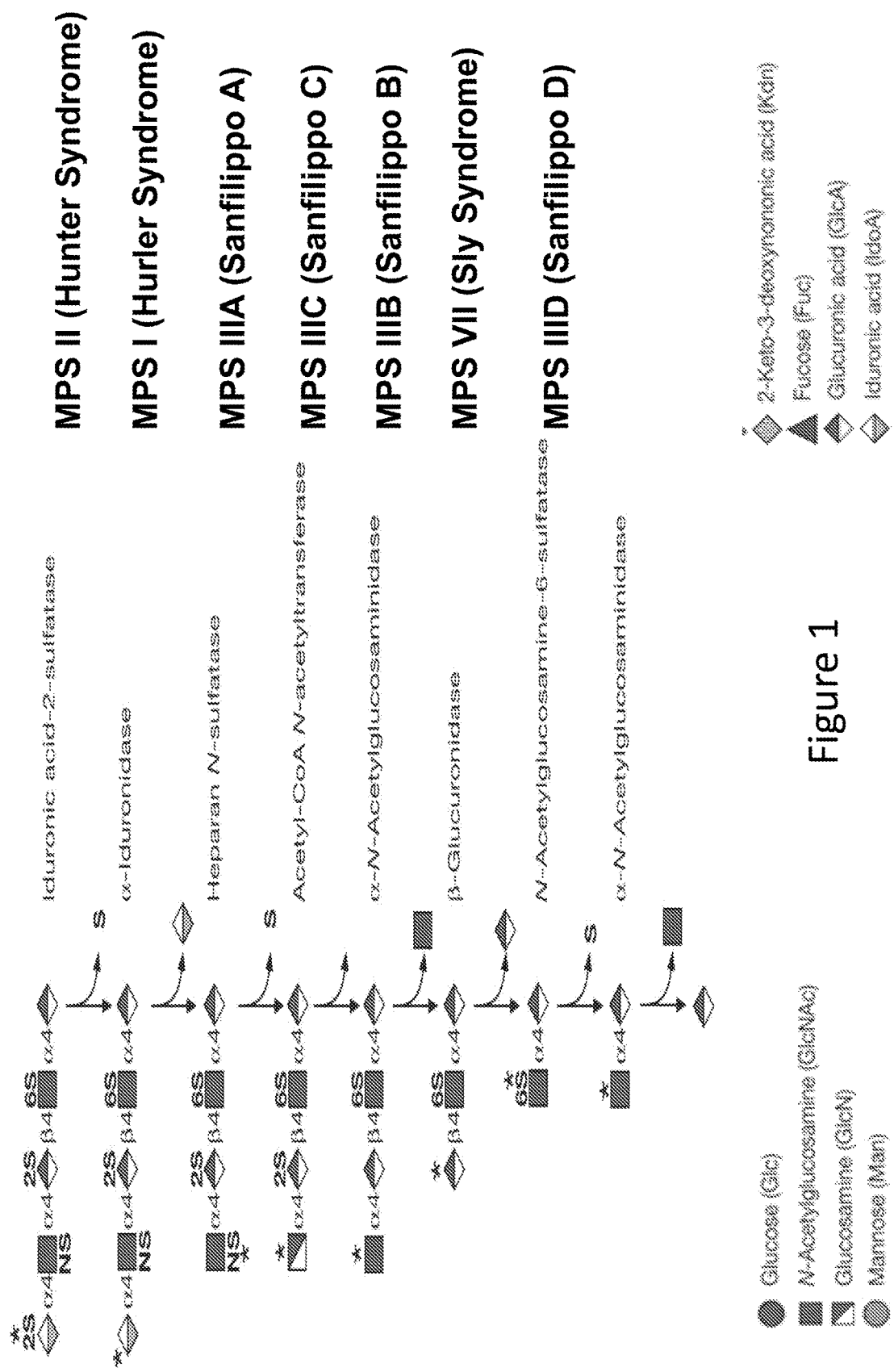
FIG. 1 illustrates stepwise degradation of heparan sulfate along with the enzyme required for each step (adapted from Essentials of Glycobiology).

The present invention provides, among other things, improved substrate clearance assays for lysosomal enzyme that are particularly useful for measuring potency of lysosomal enzymes or other therapeutics for treatment of lysosomal storage diseases. In particular, the present invention combines a physiologically relevant substrate cell assay and an efficient scintillation based detection method. As used herein, the term "potency" incorporates cellular uptake, intracellular lysosomal trafficking and/or enzymatic activity. In some cases, quantified potency as compared to a control or a reference standard is also referred to as "relative potency".

Various aspects of the invention are described in detail in the following sections. The use of sections is not meant to limit the invention. Each section can apply to any aspect of the invention. In this application, the use of "or" means "and/or" unless stated otherwise.

Lysosomal Enzymes and Substrates

In some embodiments, inventive methods according to the present invention may be used to measure any lysosomal enzymes, in particular, those have been implicated in lysosomal storage diseases. In some embodiments, lysosomal enzymes are also referred to as replacement enzymes or therapeutic enzymes. As used herein, replacement or therapeutic enzymes may include any enzyme or protein that can act to replace at least partial activity of the deficient or missing lysosomal enzyme in a lysosomal storage disease. In some embodiments, a replacement or therapeutic enzyme is capable of reducing accumulated substance in lysosomes or that can rescue or ameliorate one or more lysosomal storage disease symptoms.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Some of these and their respective substrate are exemplified in the Table below:

TABLE 1

Exemplary lysosomal enzyme and substrates

| Disease Name | Enzyme Deficiency | Substance Stored/ Physiological Substrate |
| --- | --- | --- |
| Pompe Disease | Acid-α1,4-Glucosidase | Glycogen α-1,4 linked Oligosaccharides |
| GM1 Gangliodsidosis | β-Galactosidase | GM$_1$ Gangliosides |
| Tay-Sachs Disease | β-Hexosaminidase A | GM$_2$ Ganglioside |

TABLE 1-continued

Exemplary lysosomal enzyme and substrates

| Disease Name | Enzyme Deficiency | Substance Stored/ Physiological Substrate |
| --- | --- | --- |
| GM2 Gangliosidosis: AB Variant | GM$_2$ Activator Protein | GM$_2$ Ganglioside |
| Sandhoff Disease | β-Hexosaminidase A&B | GM$_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo syndrome type A (MPS IIIA) | Heparan N-Sulfatase | Heparan Sulfate |
| Sanfilippo syndrome type B (MPS IIIB) | α-N-Acetylglucosaminidase | Heparan Sulfate |
| Sanfilippo syndrome type C (MPS IIIC) | Acetyl-CoA-Glucosaminide Acetyltransferase | Heparan Sulfate |
| Sanfilippo syndrome type D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-Mannosidase | Mannose/ Oligosaccharides |
| β-Mannosidosis | β-Mannosidase | Mannose/ Oligosaccharides |
| Fucosidosis | α-L-Fucosidase | Fucosyl Oligosaccharides |
| Aspartyl-glucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

Generally speaking, physiologically relevant substrates for lysosomal enzymes are lipids and glycoproteins also known as mucopolysaccharides or glycosaminoglycans (GAGs). As used herein, the term "physiologically relevant substrate" refers to a substrate of a lysosomal enzyme that accumulates in a patient who is deficient of the enzyme. In this application, the terms "substrate" and "physiologically relevant substrate" are used interchangeably unless it is specifically indicated otherwise.

Typically, GAGs are long unbranched polysaccharides composed of a repeating disaccharide unit. As shown in Table 1, one type of GAG involved in mucopolysaccharidosis is heparan sulfate. Normal heparan sulfate clearance requires stepwise degradation of the oligosaccharide chains at the terminal non-reducing end by a number of lysosomal enzymes including, but not limited to, iduronic acid-2-sulfatase, α-iduronidase, heparan N-sulfatase, acetyl-CoA N-acetyltransferase, α-N-acetylglucosaminidase, β-glucuronidase, N-acetylglucosamine-6-sulfatase. The stepwise degradation of heparan sulfate is diagrammed in FIG. 1 along with the enzyme required for each step (adapted from Essentials of Glycobiology). Thus, in some embodiments, the present invention may be used to measure a sulfatase including, but not limited to, various specific sulfatases described herein.

In some embodiments, the present invention may be used to measure naturally occurring lysosomal enzymes including those endogenous enzymes obtained directly from natural sources (e.g., from cells, animals, plants, or patients). In some embodiments, the present invention may be used to measure lysosomal enzymes recombinantly or chemically produced by any available means including, but not limited to, lysosomal enzymes recombinantly produced by utilizing a host cell system engineered to express a replacement enzyme-encoding nucleic acid, or lysosomal enzymes produced by activating endogenous genes, or lysosomal enzymes partially or fully prepared by chemical synthesis. In some embodiments, the present invention may be used to measure lysosomal enzymes fused or conjugated to a lysosomal targeting moiety (e.g., IGF-I, IGF-II, RAP, p97, and variants, homologues or fragments thereof) and/or with modified glycosylation pattern (e.g., increased or reduced M6P or bis-M6P levels).

Labeling Physiological Substrates

Typically, a physiologically relevant substrate suitable for the present invention is labeled with a detectable signal to facilitate detection. In some embodiments, a physiologically relevant substrate particularly suitable for the present invention is labeled with a detectable signal cleavable by a lysosomal enzyme of interest. Various methods may be used to synthesize and label a physiological substrate. In particular embodiments, a physiologically relevant substrate is synthesized by a cell or an organism and incorporates a detectable signal during synthesis. As a non-limiting example, a cell based system is illustrated below.

Cells

Various cell types may be used to synthesize physiological substrate suitable for the present invention. Suitable cells may be both adherent or non-adherent cell types. This includes primary cells and immortalized cell-lines, including those cells that have been used for standard recombinant technology.

A particularly useful cell type is a cell type where a substrate for a lysosomal enzyme of interest accumulates, for example, a cell type that can synthesize but cannot degrade or fully degrade a substrate. Thus, in some embodiments, suitable cells for the present invention are cells that are deficient in a lysosomal enzyme of interest (e.g., a sulfatase). For example, cells suitable for the present invention may lack a lysosomal enzyme of interest or have reduced enzyme activity or expression. In some embodiments, suitable cells are derived from human patients or other organisms (e.g., non-human animals such as primates, rats, mice, dogs, pigs, sheeps, etc.) that suffer from a lysosomal storage disease resulted from deficiency of a lysosomal enzyme of interest. Suitable cells may be derived from tissue sources including, but not limited to, brain, liver, lung, heart, kidney, skin, muscle. Suitable cells may also be epithelial, endothelial, mesenchymal, and neuroectodermal cells. In certain embodiments, suitable cells are fibroblasts derived from human patients or other organisms. In certain other embodiments, suitable cells are neurons derived from human patients or other organisms.

In some embodiments, suitable cells may also be generated by depleting an endogenous lysosomal enzyme of interest by standard gene knock out technology or by anti-sense or interfering RNA technology. Such suitable cells may be prokaryotic (e.g., bacteria) or eukaryotic cells including plant, yeast, or mammalian cells. Non-limiting examples of mammalian cells that may be used in accordance with the present invention include BALB/c mouse myeloma line (NSO/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Labeled, Cell Synthesized Substrate

In general, labeling a cell synthesized substrate involves growing suitable cells described herein in the presence of a substance or reagent that can be incorporated into the substrate to provide a detectable signal. In some embodiments, cells are thawed from a frozen state and expanded under standard cell culture conditions to a pre-determined desired cell density. Suitable cell density may be determined by confluency. For example, a suitable cell density may be at least about 20%, 25%, 30%, 35%, 40%, 45%, 50%, 55%, 60%, 65%, 70%, 75%, 80%, 85%, 90%, 95%, 96%, 97%, 98%, 99% or 100% confluent. In some embodiments, a suitable cell density may be in the range of approximately 25% to 100%, 30% to 95%, 35% to 90%, 40% to 85%, 45% to 80%, 50% to 75%, 50% to 99%, 50% to 98%, 50% to 97%, 50% to 96%, 60% to 99%, 60% to 98%, 60% to 97%, 60% to 96%, 70% to 99%, 70% to 98%, 70% to 97%, 70% to 96%, 80% to 99%, 80% to 98%, 80% to 97%, 80% to 96%, 40% to 50%, 45% to 55%, 50% to 60%, 55% to 65%, 60% to 70%, 65% to 75%, 70% to 80%, 75% to 85%, 80% to 90%, 85% to 95%, or 90% to 100% confluent. In some embodiments, suitable cell density may be up to about 50%, 55%, 60%, 65%, 70%, 75%, 80%, 85%, 90%, 95%, 96%, 97%, 98%, or 99% confluent. In some embodiments, a suitable cell density may be determined by the cell numbers per well (e.g., per well of a 6, 12, 24, 48 or 96-well plate). For example, a suitable cell density may be at least about 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 12,500, 15,000, 17,500, 20,000, 22,500, 25,000, 27,500, 30,000, 35,000, 40,000, 45,000, 50,000, 55,000, 60,000, 65,000, 70,000, 75,000, 80,000, 85,000, 90,000, 95,000, 100,000 cells per well. In some embodiments, a suitable cell density may be in the range of approximately 500-100,000 cells per well; 1,000-90,000 cells per well; 2,000-80,000 cells per well; 3,000-70,000 cells per well; 4,000-60,000 cells per well; 5,000-50,000 cells per well; 6,000-40,000 cells per well; 7,000-30,000 cells per well; 8,000-27,500 cells per well; 9,000-25,000 cells per well; 10,000-25,000 cells per well; 12,500-25,000 cells per well; 15,000-25,000 cells per well; 15,000-22,500 cells per well; or 15,000-20,000 cells per well. In some embodiments, a suitable cell density may be up to about 5,000, 5,500, 6,000, 6,500, 7,000, 7,500, 8,000, 8,500, 9,000, 9,500, 10,000, 12,500, 15,000, 17,500, 20,000, 22,500, 25,000, 27,500, 30,000, 35,000, 40,000, 45,000, 50,000, 55,000, 60,000, 65,000, 70,000, 75,000, 80,000, 85,000, 90,000, 95,000, 100,000 cells per well.

The cells are then treated with a substance or reagent that can be incorporated into a newly synthesized substrate and emit detectable signal. In some embodiments, such suitable substance or reagent provides radioactive isotopes that can be incorporated into a newly synthesized substrate. In some embodiments, suitable radioactive isotopes include those isotopes that emit electrons having a mean range up to 2000 μm in aqueous media. As non-limiting examples, suitable radioactive isotopes include $^3H$, $^{125}I$, $^{14}C$, $^{35}S$, $^{45}Ca$, $^{33}P$, $^{32}P$, $^{55}Fe$, $^{109}Cd$, and $^{51}Cr$.

In some embodiments, a $^{35}S$-containing substance or reagent is used to generate radiolabeled physiological substrate synthesized by cells, such as GAGs. As a non-limiting example, $^{35}S$-sodium sulfate may be added to growth medium at a desired cell density (e.g., about 95% confluent) to generate radiolabeled GAGs (e.g., radiolabeled heparan sulfate).

Attachment to Scintillant Base

Cells containing radiolabeled substrate may be seeded into a vessel that contains a scintillant base such that the cells may attach to the scintillant base. Any vessel that can be used to grow cells and have a scintillating base is suitable for this invention. This includes flasks, Petri dishes, conical vials, disposable bags and multi-well plates. At least one surface of the vessel acts as a scintillant base (also referred to as a scintillating base plate or scintillant layer), which contains scintillator material that exhibits luminescence when excited by ionizing radiation. Typically, the scintillating base plate or disc, like all plastic tissue culture ware, requires surface modification in order to be adapted for the attachment and/or growth of cells. Treatment preferably involves the use of high voltage plasma discharge, a well-established method for creating a negatively charged plastic surface (Arnstein, C. F. and Hartmann, P. A, J. Clinical Microbial., 2,1, 46-54, (1975)). For many cell types, this surface is suitable for both growth and assay purposes. However, cell attachment or growth can be further improved by applying a range of additional coatings to the culture surface of the device. These can include: (i) positively or negatively charged chemical coatings such as poly-lysine or other biopolymers (McKeehan, W. L. and Ham, R. G., J. Cell Bioi., 71, 727-734, (1976)); (ii) components of the extracellular matrix including collagen, laminin, fibronectin (Kleinman, H. K. et al, Anal. Biochem., 166, 1-13, (1987)) and (iii) naturally secreted extracellular matrix laid down by cells cultured on the plastic surface (Freshney, R. I.). Furthermore, the scintillating base plate may be coated with agents such as lectins, or adhesion molecules to enable the attachment of cell membranes or cell types that normally grow in suspension. Methods for the coating of plasticware with such agents have been described previously, see for example, Boldt, D. T. and Lyons, R. D., J. Immunol., 123, 808, (1979)).

A suitable scintillant base is preferably optically transparent, both to allow cells in culture to be viewed using an inverted phase contrast microscope, and to enable the material to transmit light at a given wavelength with maximum efficiency. In addition, the base retains its optical properties even after exposure to incident beta radiation from radio-isotopes as well as under stringent radiation conditions required for sterilization of the plates.

A suitable scintillant base can be composed of any transparent material containing scintillant, e.g. a scintillant glass based on lanthanide metal compounds. In certain formats, a base plate is composed of any plastic material, where normally the monomer units which comprise the polymer include phenyl or naphthyl moieties, in order to absorb incident radiation energy from radionuclides which are in close proximity with the surface. An exemplary plastic base plate is composed of polystyrene or polyvinyltoluene, into which is incorporated a scintillant substance. A suitable scintillant substance can include aromatic hydrocarbons such as p-terphenyl, p-quaterphenyl and their derivatives, as well as derivatives of the oxazoles and 1,3,4-oxadiazoles, such as 2-(4-t-butylphenyl)-5-(4-biphenylyl)-1,3,4-oxadiazole and 2,5-diphenyloxazole. Also included in the polymeric composition may be a wavelength shifter such as 1,4-bis(5-pheny-2-xazolyl)benzene, 9,10-diphenylanthracene, 1,4-bis (2-methylstyryl)-benzene etc. The function of the wavelength shifter is to absorb the light emitted by the scintillant substance and re-emit longer wavelength light which is a better match to the photo-sensitive detectors used in scintillation counters.

Additional devices with a scintillant base suitable for the invention and methods making and using the same are described, for example, in U.S. Pat. Nos. 5,665,562, and 5,989,854, each incorporated herein by reference.

According to the invention, radioactive emissions emitted by radiolabeled physiological substrate synthesized by cells attached or adhered to a scintillant base are close enough to the scintillant base to cause light emissions which may be detected by the detection means for observing scintillation events. In some embodiments, decay of radiolabeled physiological substrate synthesized by the cells emits electrons (e.g., with a mean range up to 2000 μm (e.g., up to 1800 μm, 1600 μm, 1400 μm, 1200 μm, 1000 μm, 800 μm, 600 μm, 400 μm, or 200 μm) in aqueous media, which are sufficient to cause scintillation events detectable by standard detection means such as beta counter. Unbound or free radiolabel in the growth medium is generally too far away from the surface of the scintillant base of the well, the radiation energy being dissipated into the aqueous environment and the radioactive disintegrations will remain undetected by the detector. Thus, scintillation events generated by a scintillant base are indicative of the radioactive emission level associated with the cells attached or adhered to the base, which, in turn, is indicative of the amount of radiolabeled physiological substrate within the cells. A baseline radioactive emission level associated with the cells containing radiolabeled substrate may be measured before the addition of a lysosomal enzyme.

Apparatus and method for the measurement of scintillation events may involve real time measurement using non-invasive techniques, that is to say techniques that do not compromise the integrity or viability of the cells. Various beta counters such as the Microbeta 2 beta counter (manufactured by PerkinElmer) may be used to practice the invention.

Substrate Clearance Assay

Once a layer of cells are adhered or attached to a scintillant base, a sample containing a lysosomal enzyme of interest may be added to perform a substrate clearance assay. In some embodiments, a suitable sample may contain a purified lysosomal enzyme. For example, a suitable sample may be a sample of formulated drug product containing a lysosomal enzyme of interest. A suitable sample may also contain a partially purified or un-purified lysosomal enzyme. For example, a cell culture medium sample obtained from a recombinant manufacturing process containing a lysosomal enzyme of interest secreted from cultured cells may be directly used in clearance assays according to the present invention. Alternatively, a lysate of recombinant cells producing a lysosomal enzyme of interest may be used. In some embodiments, a sample obtained from a purification process may be used, such as, for example, an eluate or pooled eluates from chromatography and/or filtration steps. In some embodiments, a suitable sample may be a biological sample directly taken from a patient including, but not limited to, a blood sample, a cerebrospinal fluid (CSF) sample, a urine sample, and a tissue extract from a solid organ (e.g., brain, liver, lung, heart, kidney, skin, or muscle). In some embodiments, multiple samples with titrating amounts of enzyme may be assayed simultaneously to generate a dose-response curve to facilitate calculating relative potency of the enzyme.

Typically, samples containing a lysosomal enzyme and cells are incubated under conditions that allow the lysosomal enzyme be internalized and properly delivered to lysosomes so that the lysosomal enzyme can act to degrade the accumulated substrate to remove radioactive isotope from the substrate. Typically, standard cell culture conditions may be used for this purpose. For example, cells may be incubated at 37° C. in an incubator containing a humidified 95% air/5% $CO_2$ atmosphere for a pre-determined period of time (e.g., about 5 minutes, 10 minutes, 15 minutes, 20 minutes, 25 minutes, 30 minutes, 60 minutes, 2 hours, 6 hours, 8 hours, 10 hours, 15 hours, 20 hours, 25 hours, 30 hours, 35 hours or longer).

It is contemplated that degradation of a radiolabeled substrate (e.g., $^{35}S$ labeled GAGs) lead to cleavage of radioactive isotopes (e.g., $^{35}S$) from the substrate. As a result, cleaved radioactive isotopes are released from the cells into the growth medium. It is further contemplated that the decay of the free radiolabel in the growth medium is too distant from the scintillant base to produce signals (e.g., scintillation events) and only the decay of the remaining un-degraded radiolabeled substrate within the cells will continue to emit signals. Accordingly, a reduction of radioactive emission level associated with the cells is indicative of the potency of the lysosomal enzyme. Lower radioactive signal associated with the remaining substrate within the cells is indicative of greater amounts of internalized, active enzyme (i.e., greater potency).

Since free radiolabel in the growth medium is too distant from the scintillant base to produce signals (e.g., scintillation events), the present invention does not involve extensive wash steps before measuring remaining radioactive emission signals. In some embodiments, however, a wash step is performed before the step of measuring remaining radioactive emission signals.

In some embodiments, a clearance study according to the invention may be used to characterize cellular uptake, intracellular lysosomal trafficking and/or enzymatic activity. For example, to characterize cellular uptake (i.e., internalization) process, a clearance assay according to the present invention may be performed in the presence of a candidate inhibitor of uptake. In some embodiments, to determine if cellular uptake (i.e., internalization) occurs via mannose-6-phosphate receptor, a clearance assay described herein may be performed with or without M6P residues added to the growth medium together with the sample. If the presence of M6P residue reduces the reduction of radioactive emission levels associated with the cells, it indicates that the cellular uptake process is dependent on the mannose-6-phosphate receptor. Similarly, IGF-I, IGF-II, RAP, or p97 may be used as candidate inhibitors to determine if cellular uptake (i.e., internalization) occurs via any of these peptide targeting moieties respectively. In some embodiments, a clearance assay according to the present invention may be used to characterize cellular uptake that occurs through other receptors including, but not limited to, the insulin receptor or the LDL receptor.

High Throughput Format

In some embodiments, substrate clearance assays in accordance with the present invention can be carried out on high throughput platforms. High throughput platforms are particularly useful for performing assays with multiple samples simultaneously. In certain embodiments, high throughput assays may include steps of: (a) providing cells where GAGs accumulate as described herein into a plurality of wells with a scintillant base such that the cells attach or adhere to the scintillant base, (b) providing a plurality of samples containing a lysosomal enzyme of interest, simultaneously or sequentially, to the plurality of wells containing the cells, (c) conducting substrate clearance assays as described herein, and (d) measuring and collecting radioactive emission signal from each of the plurality of the wells, simultaneously or sequentially, to determine relative potency of lysosomal enzymes. In some embodiments, multiwell plates, e.g., 6-, 12-, 24-, 48-, 96-, 384-, or 1536-well plates, may be used for high throughput assays. In some embodiments, 96-well Cytostar T™ scintillating plates (manufactured by PerkinElmer) may be used.

Data Analysis and Quantification

In some embodiments, scintillation data is collected from a scintillation plate containing cells that have incorporated a radioisotope into newly formed substrate (e.g., GAGs) both before and after an enzyme is added to each well. As the enzyme is internalized by the cells, it cleaves the radiolabeled GAGs, which are released from the cells. Generally speaking, a reduced radioisotope signal detected by a scintillation detector after enzyme treatment as compared to the baseline signal is indicative of a potent enzyme being internalized and delivered to lysosomal enzyme. A lower signal is indicative of greater amount of internalized and functional enzyme (e.g., greater potency).

In some embodiments, the potency of a lysosomal enzyme may be quantified as compared to a control. As used herein, a quantified potency relative to a control is also referred to as relative potency. In some embodiments, a suitable control is a reference standard indicative of a predetermined potency of a lysosomal enzyme of interest. A relative potency can be determined by taking the ratio of potency of a sample and the potency of a reference lot. This can be accomplished by either determining the potency of reference lot and sample independently and then taking the ratio or by doing a parallel line analysis using equivalence or an f-test. Available standard curve fitting software such as Graph Pad Prism, Excel-fit, Stegmann PLA, StatLIA, to name but a few, can be used for data analysis. In some embodiments, a suitable control is a radioactive emission level obtained from a control sample containing a known amount of lysosomal enzyme of interest using the same assay. In some embodiments, a suitable control is a dose-response curve obtained by running the same assay with titrating amounts of enzyme. In some embodiments, a combination of one or more of the above controls are used.

In some embodiments, multi-well plates are used so that scintillation data (i.e. radioisotope signal) can be simultaneously collected from one or more test samples, one or more control or standard samples, and/or multiple titrating samples with a serial dilution of enzyme concentration. Various software for data analysis is available in the art and can be used to analyze data, quantify and calculate relative potency. In some embodiments, a multi-parameter logistic curve fit can be used to analyze the data. In some embodiments, suitable parameters of the curve that can be used to analyze the data include, but not limited to, the top of the curve, the bottom of the curve, the slope of the curve, the inflection point of the curve, the EC 50 determined from the curve or a combination of these parameters. Any 2, 3, 4, 5, or more of the suitable parameters may be used. For example, a 4 parameter logistic curve can be fit for each reference standard, control and test sample. An equivalence test for parallelism based on the difference between the slope parameters from each pair of curves being compared is performed. If the test for parallelism is passed, a restricted model (shared slope and upper and lower asymptote parameters) is fit to both curves, allowing a relative potency to be calculated.

Linearity of a bioassay is the assay's ability to obtain test results that are directly proportional to biological potency over a given range. To determine linearity, "known" samples of various potencies may be generated by pre-diluting reference standard to a specified concentration. In this way, dilutional linearity is used as a surrogate for potency. Plotting the data from dilutional linearity samples with expected relative potency values on the X axis and observed relative potencies on the Y axis and fitting the data to a linear regression provides an estimation of linearity. As shown in the Examples, the platform assay according to the present invention has an unexpected wide range of linearity range. In some embodiments, an assay according to the present invention is linear over a range of about 10-400%, 20-350%, 30-300%, 40-250%, or 50-200% relative potency. In other embodiments, an assay according to the present invention is linear over a range of about 40-240% relative potency.

In some embodiments, the total amount of a lysosomal enzyme in each sample is determined to normalize the potency calculated.

Applications

Among other things, the present invention provides a simple and reliable quality control tool for sample characterization and/or process development. For example, the present invention may be particularly useful in evaluating potency of a lysosomal enzyme or other biologics during the manufacturing and/or purification process. In some embodiments, a process for manufacturing a lysosomal enzyme may include a quality control step by determining the potency of the lysosomal enzyme using a substrate clearance assay described herein. For example, such quality control step based on the determination of the potency of the lysosomal enzyme may be performed before releasing a lot from a manufacturing process. The present invention may also be used to compare or evaluate change in enzyme potency through the course of process development. Two or more samples from different culture processes may be tested using substrate clearance assays described herein multiple times at multiple time points. In this case, a sample from one manufacturing process may be used as a control for another sample from a different process. In some embodiments, based on the enzyme potency determined according to the present invention, one or more manufacturing conditions may be adjusted.

Similarly, a process for purifying a lysosomal enzyme may include a step of determining the potency of the lysosomal enzyme using a substrate clearance assay described herein. For example, such a step may be performed before releasing a purified lot. The present invention may also be used to compare or evaluate change in enzyme potency through the course of purification process development. Two or more samples from different purification processes may be tested using substrate clearance assays described herein multiple times at multiple time points. In this case, a sample from one purification process may be used as a control for another sample from a different process. In some embodiments, based on the enzyme potency determined according to the present invention, one or more purification conditions may be adjusted.

In addition, the present invention may be used to characterize and/or standardize the potency of a lysosomal enzyme or other therapeutics for product approval, labeling, and/or packaging.

Furthermore, the present invention may also be used to assess enzyme potency in a biological sample directly obtained from patients for diagnosis and therapy monitoring purposes.

EXAMPLES

Example 1—GAG Substrate Clearance Assay

This example illustrates an exemplary process for labeling cell synthesized physiological substrate (e.g., GAGs), enzyme clearance assay, and data analysis for determining relative potency according to the present invention.

Label Cell Synthesized GAGs

On the first week of the assay, patient fibroblasts (a cell type where GAGs accumulate) are thawed and then grown until the cells have expanded to a predetermined cell density. Then, starting on Day 14, 95% confluent patient cells were treated with 1 mCi $^{35}$S-Sodium sulfate for 48 hours so that they incorporated the radioisotope into newly formed GAGs. The cells were then seeded into 96-well Cytostar T™ (PerkinElmer) scintillation plates at 25,000 cells/well. Once attached to the scintillation plates, the cells were simultaneously dosed with titrated amounts of enzyme. They were then incubated at 37° C. and at 5% $CO_2$. Once the enzyme was internalized, it cleaved the radiolabeled GAGs, which were released from the cells and washed away. The lower $^{35}$S signal is indicative of greater amounts of internalized, functional enzyme.

Data Analysis

Figure 2:
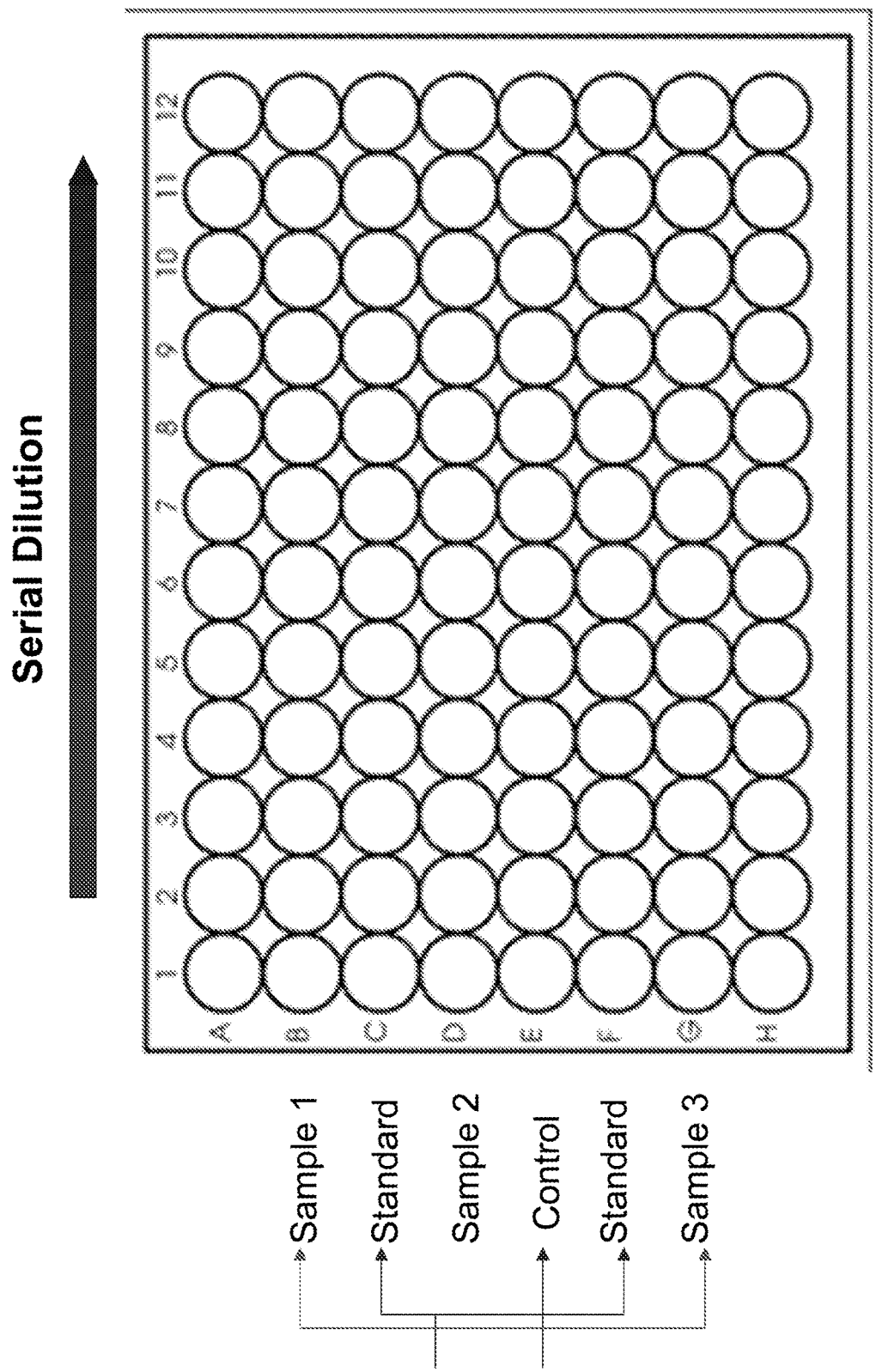
FIG. 2 shows a schematic of a 96 well plate set-up for a substrate clearance assay with one control, standards and three samples distributed among rows B through G, with each row treated with a serial dilution of enzyme concentration from column 1 to 12.
Figure 3:
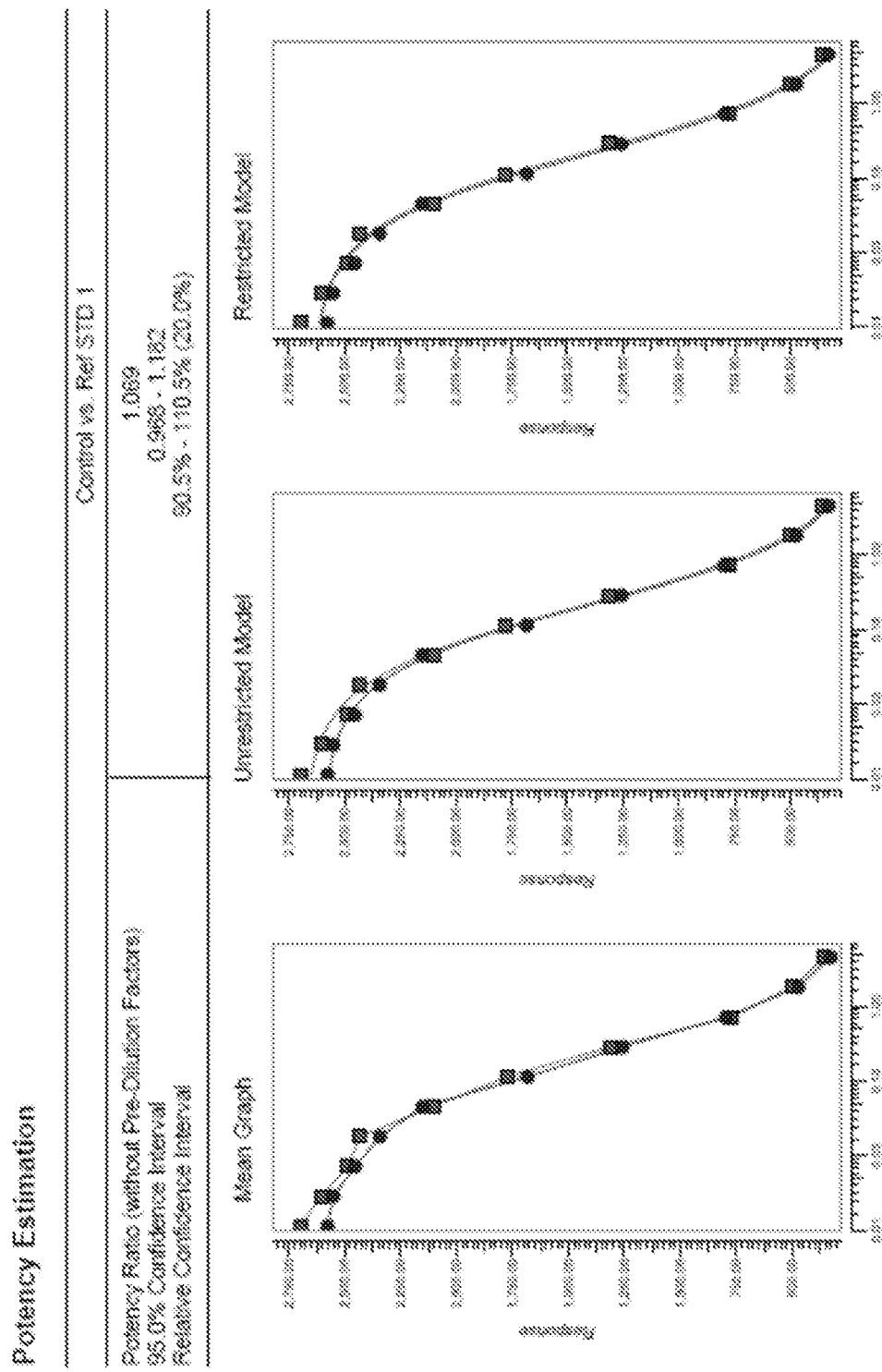
FIG. 3 depicts exemplary graphs for data analysis for a GAG substrate clearance assay, with potency estimated using a 4-parameter logistic curve fit.
Figure 4A:
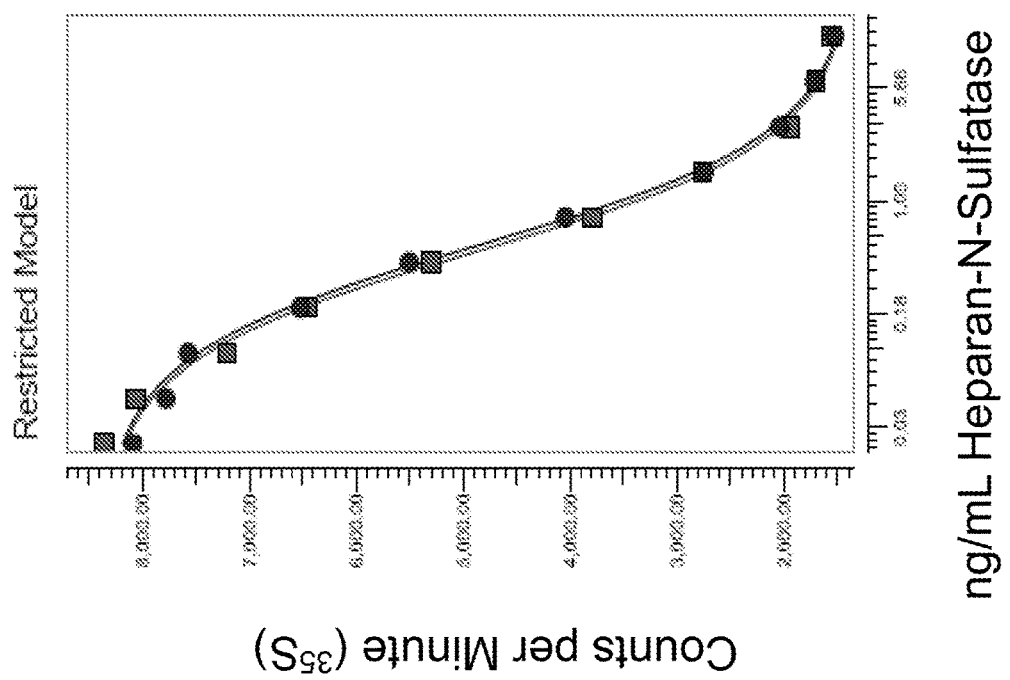
FIG. 4 depicts exemplary graphs for data analysis for a GAG substrate clearance assay, using the enzymes heparan N-sulfatase (FIG. 4A), iduronate-2-sulfatase (FIG. 4B) and N-aceylglucosaminidase (FIG. 4C).
Figure 4B:
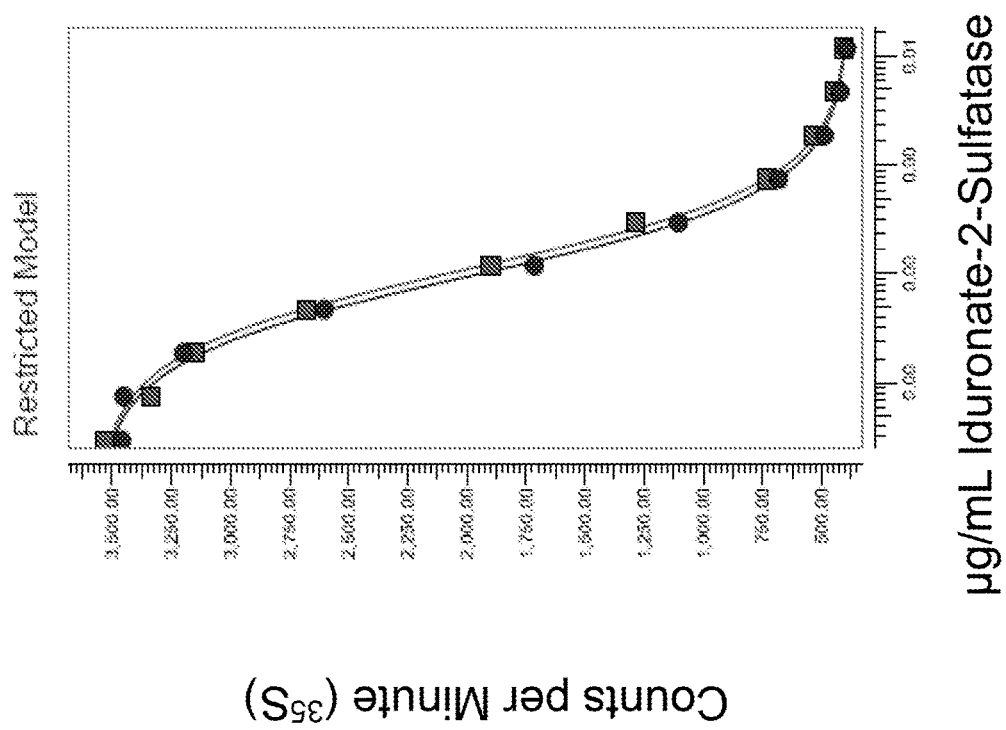
Figure 4C:
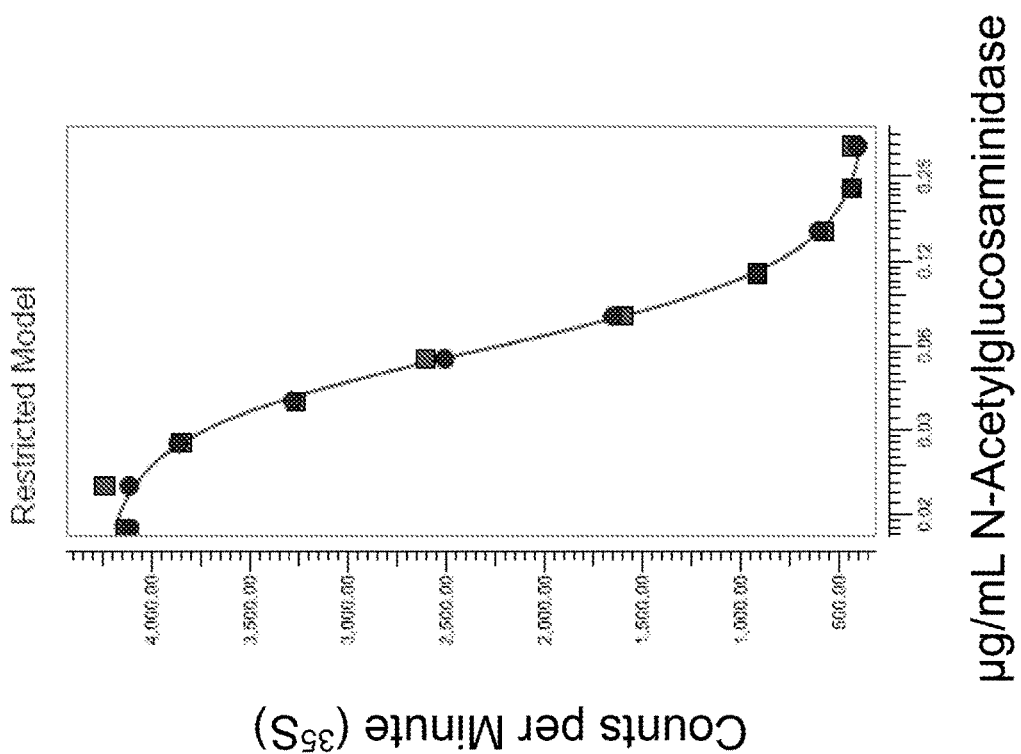

This substrate clearance assay measures relative potency, incorporating uptake, proper intracellular lysosomal trafficking and enzyme activity. On one 96-well plate, a control, multiple standards and multiple samples can be run at a serial dilution of enzyme concentration (FIG. 2). A 4 parameter logistic curve is fit for each reference standard, control and test sample. An equivalence test for parallelism based on the difference between the slope parameters from each pair of curves being compared is performed and if the test for parallelism is passed, a restricted model (shared slope and upper and lower asymptote parameters) is fit to both curves, which allows a relative potency to be calculated (FIGS. 3 and 4).

Linearity

Figure 5:
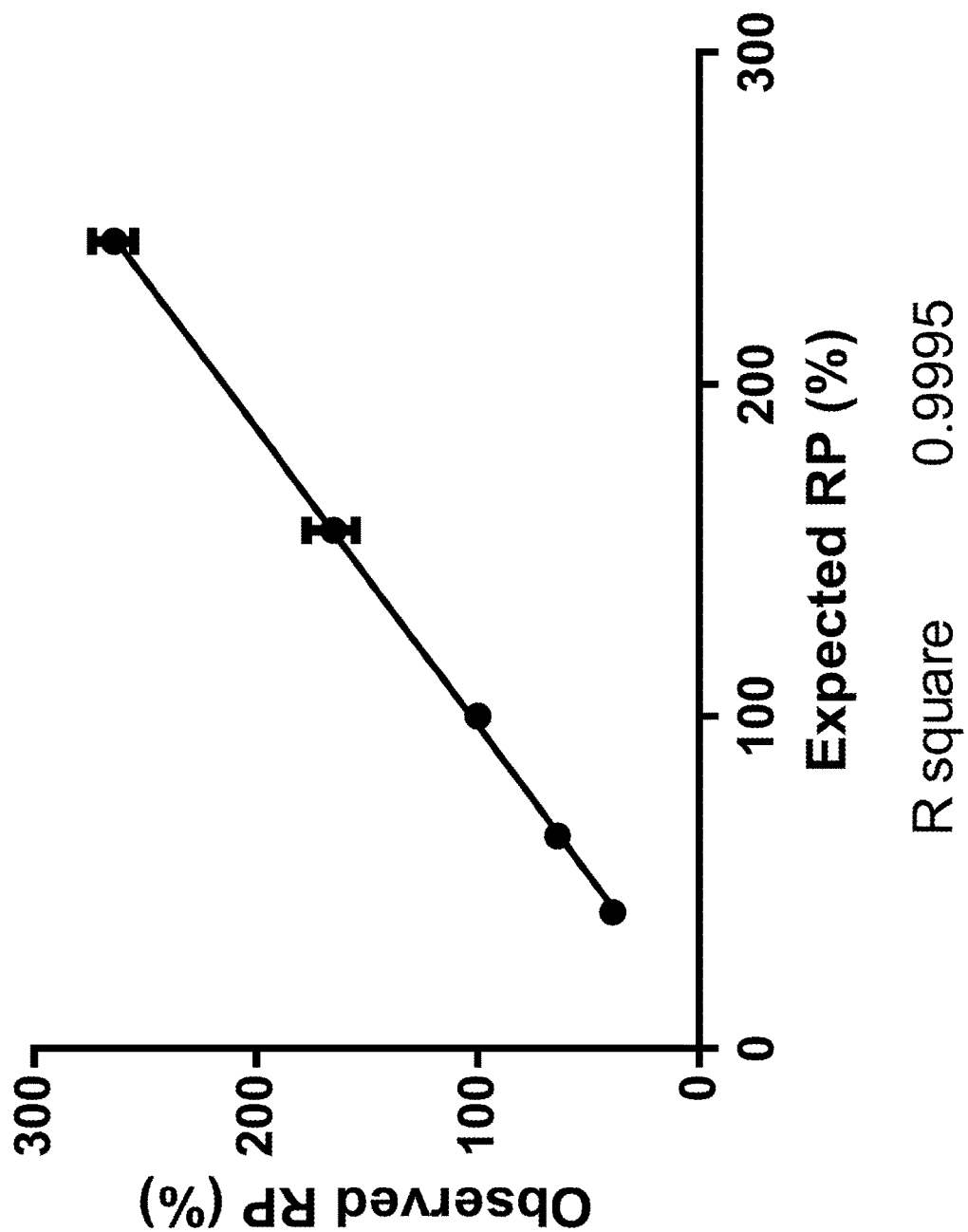
FIG. 5 depicts an exemplary graph that demonstrates accuracy in relative potency over a wide linearity range.
Figure 6A:
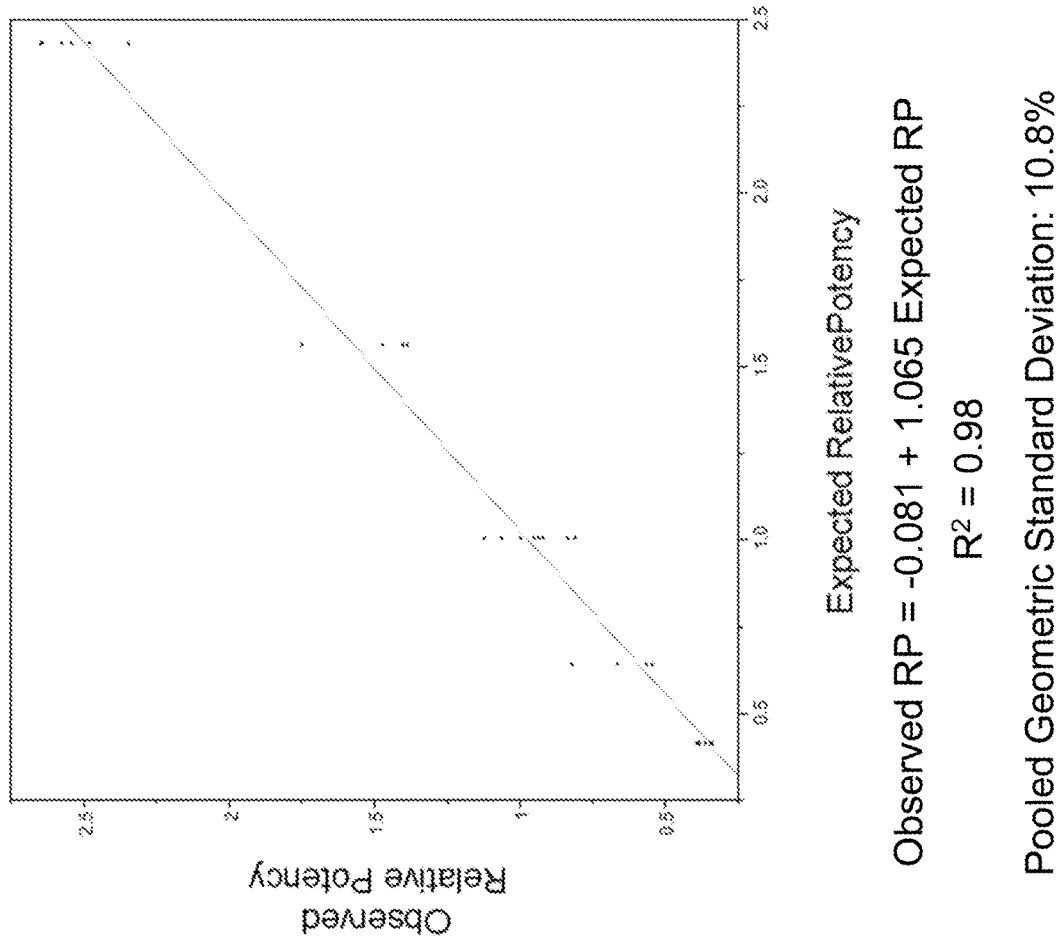
FIG. 6 depicts exemplary graphs that demonstrates accuracy in relative potency of GAG clearance with the enzymes heparan-N-sulfatase (FIG. 6A) and iduronate-2-sulfatase (FIG. 6B) over a wide linearity range.
Figure 6B:
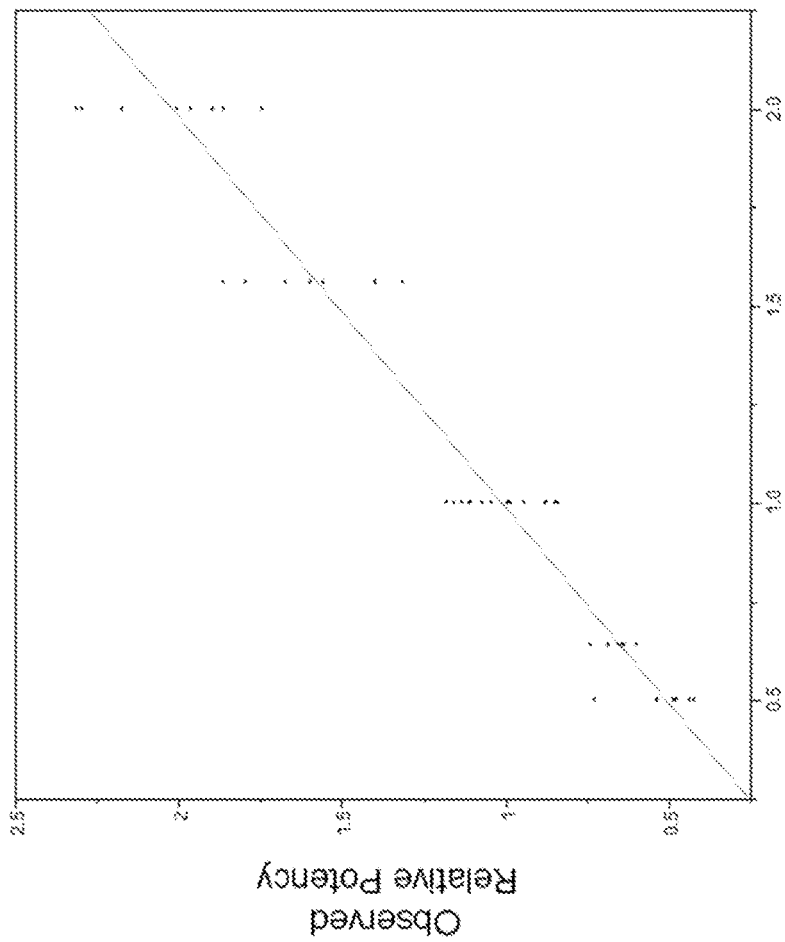

Linearity of a bioassay is the assay's ability to obtain test results that are directly proportional to biological potency over a given range. To determine linearity, "known" samples of various potencies may be generated by pre-diluting reference standard to a specified concentration. In this way, dilutional linearity is used as a surrogate for potency. Plotting the data from dilutional linearity samples with expected relative potency values on the X axis and observed relative potencies on the Y axis and fitting the data to a linear regression provides an estimation of linearity. As seen in FIGS. 5 and 6 and in Table 2, this assay demonstrates accuracy over an unexpectedly wide linearity range. Samples from 41% RP to 243% RP can be compared to each other.

To determine the precision of the assay, the assays ability to obtain accurate results despite inter- and intra-run variations multiple analysts performed a dilutional linearity test. Factors considered from run to run include day the assay is performed, analyst, cell harvest concentration, and $^{35}$S lot. The % GCV at each dilutional linearity level was calculated and an intermediate precision of 10.3% was established for this particular assay. The inter-run variance is dependent on factors such as day the assay is performed, analyst, cell harvest concentration, and $^{35}$S lot whereas the intra-run variance is dependent on factors such as effect of test sample location on plate and pipetting consistency >75% and up to 95% of variance is attributed to intra-run factors for all dilutional linearity levels. The % GCVs calculated from 41% RP to 243% RP confirm that this method is precise across the linear range, supporting a method range of 41-243% RP.

TABLE 2

| Expected RP (%) | Observed RP (%) | Accuracy (%) |
|---|---|---|
| 41 | 39 | 95 |
| 64 | 64 | 100 |
| 100 | 100 | 100 |
| 156 | 165 | 106 |
| 243 | 264 | 109 |

Reproducibility and Specificity

The data in Table 3 demonstrate reproducibility with very small variability, as can be seen with the low standard deviations. An established assay Control returns expected potency value in multiple experiments over a long period. Additionally, when an established Control is exposed to stress conditions, such as $H_2O_2$, low pH (e.g. 4.0), or photo exposure the RP % is decreased. This demonstrates that the assay is reproducible and capable of indicating stability of the enzyme over a prolonged period.

TABLE 3

| n | Sample 1 RP (%) | Sample 2 RP (%) | Sample 2 Stressed RP (%) |
|---|---|---|---|
| 1 | 98.7 | 82.0 | 39.5 |
| 2 | 103 | 84.0 | 41.8 |
| 3 | 107 | 86.1 | 41.8 |
| 4 | 114 | 87.7 | 46.2 |
| Mean | 106 | 84.9 | 42.2 |
| Stdev | 6.5 | 2.48 | 2.82 |

Mannose-6-Phosphate Dependent Cellular Uptake

Figure 7:
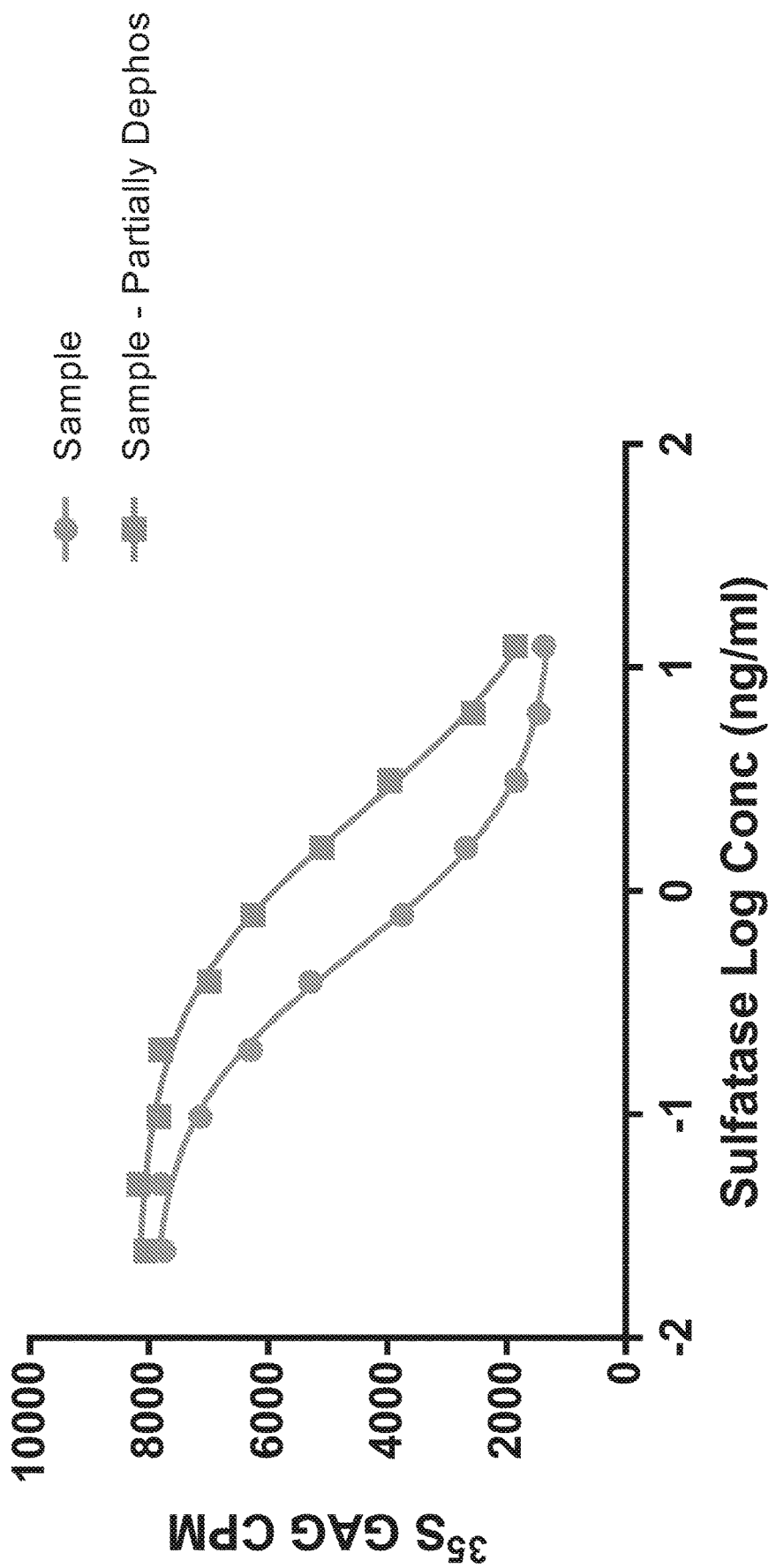
FIG. 7 depicts an exemplary graph demonstrating mannose-6-phosphate mediated internalization, with removal of phosphate from a sulfatase decreasing its activity in the GAG clearance assay.
Figure 8:
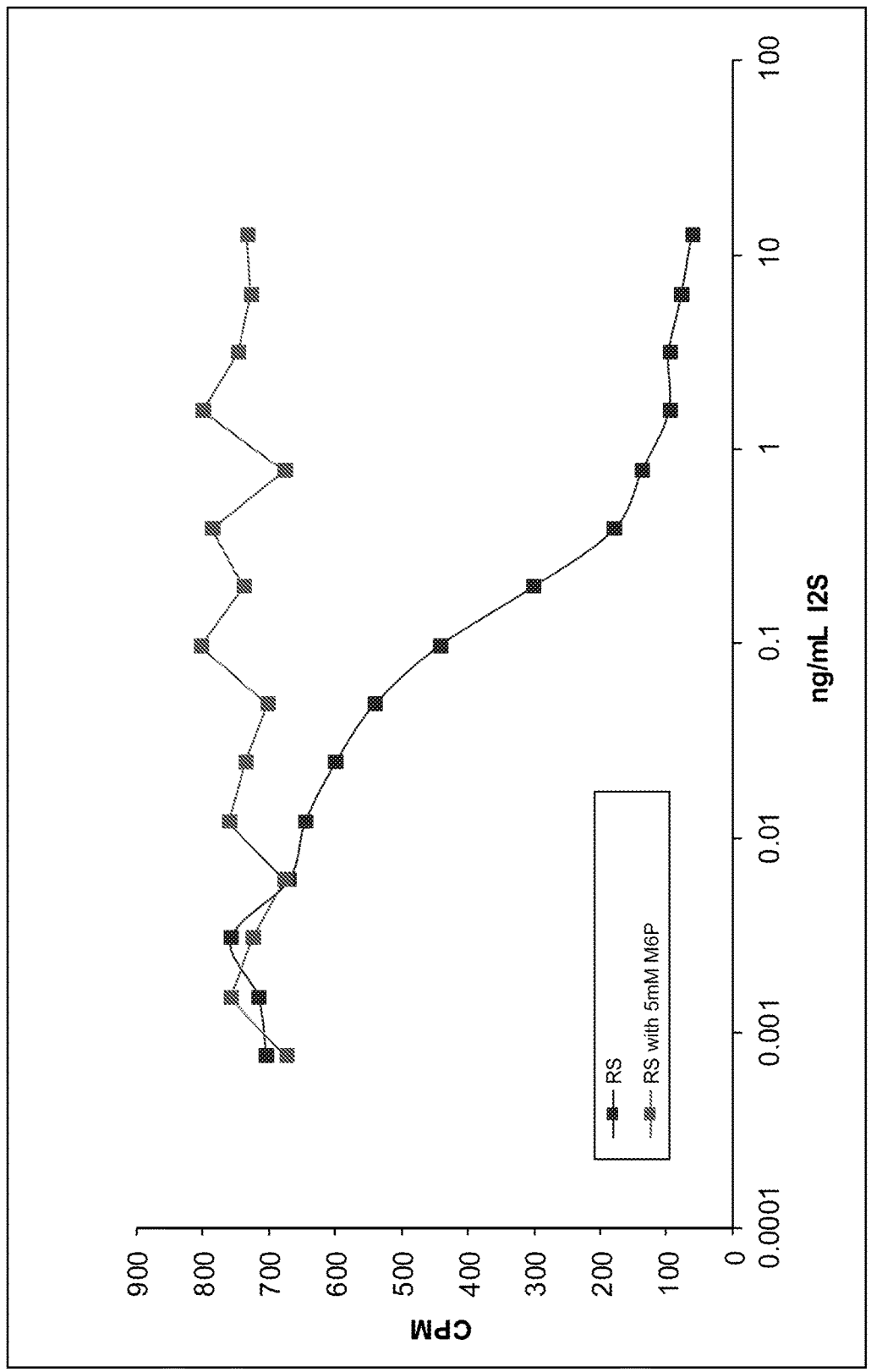
FIG. 8 depicts an exemplary graph demonstrating complete inhibition of iduronate-2-sulfatase (I2S) dependent GAG clearance in the presence of 5 mM mannose-6-phosphate. Mannose-6-phosphate binds to the mannose-6-phosphate receptor, blocking binding of the therapeutic enzyme and subsequent internalization and trafficking to the lysosome.

In this particular example to determine if internalization (or cellular uptake) occurs via the mannose-6-phosphate receptor specifically, 5 mM mannose-6-phosphate (M6P) was added to the growth medium and the GAG clearance assay was performed as described above. Mannose-6-phosphate binds to the Mannose-6-Phosphate receptor, blocking binding of the enzyme and subsequent internalization and trafficking to the lysosome. As shown in FIGS. 7 and 8, complete inhibition a sulfatase-dependent GAG clearance in the presence of 5 mM mannose-6-phosphate was observed.

Figure 9:
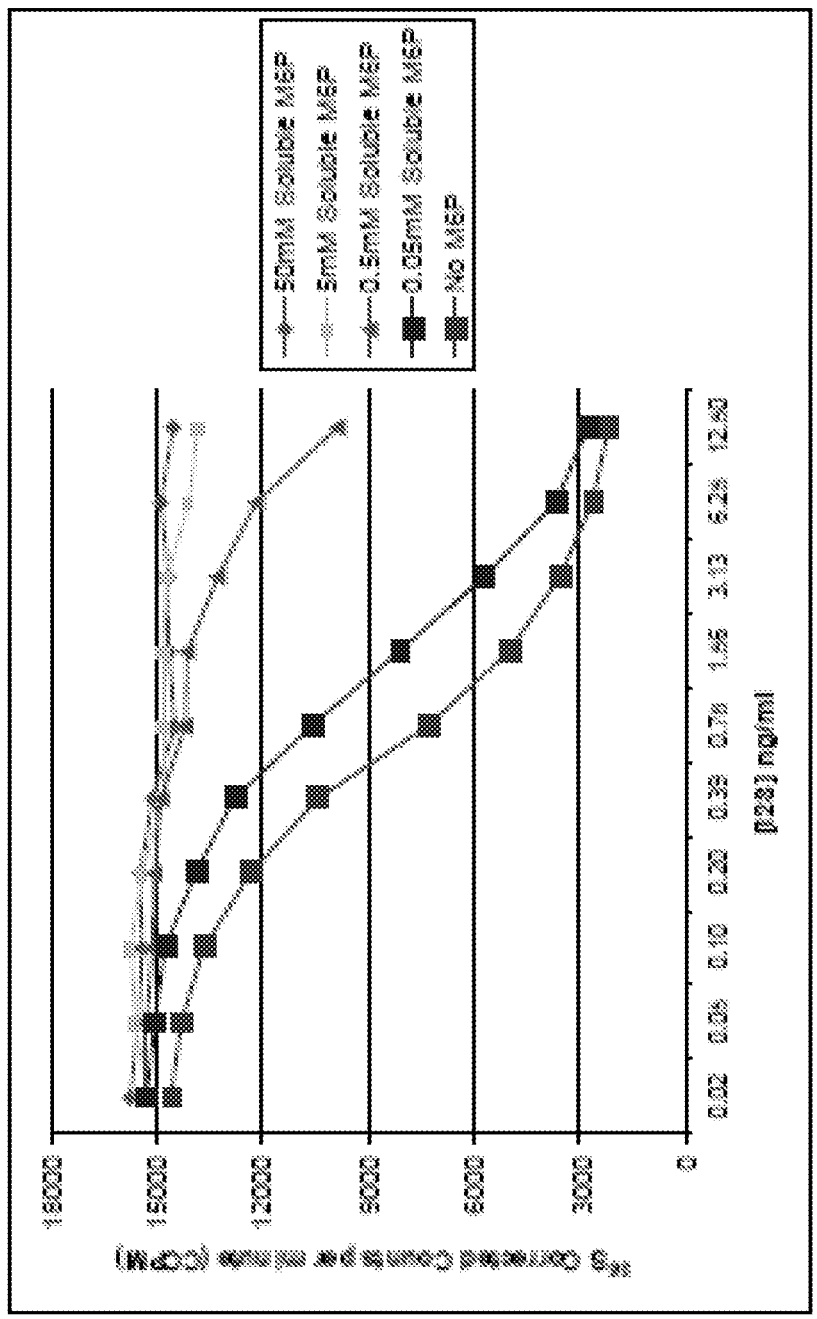
FIG. 9 depicts an exemplary graph demonstrating the mannose-6-phosphate dose dependent inhibition of iduronate-2-sulfatase (I2S) dependent GAG clearance.

In an additional example to demonstrate receptor specificity, a range of soluble M6P doses were used to compete with I2S uptake. Specificity tests demonstrated dose dependent uptake inhibition using 50, 5, 0.5, 0.05 and 0 mM M6P (FIG. 9). As high concentration of soluble M6P occupies the M6P receptor, less recombinant functional I2S enzyme uptake takes place resulting in low $^{35}$S labelled GAG clearance from cells as evident by a high assay signal. The observed inhibition of GAG clearance at high M6P concentration confirms that I2S uptake is primarily mediated bt the surface-expressed M6P receptor.

Formulation Effect

To determine if formulation buffer effects the clearance of $^{35}$S labelled GAGs, recombinant I2S was suspended in three different formulation buffers and the GAG clearance assay was performed as described above. As shown in Table 4 below, none of the formulations tested demonstrated measurable effects on the clearance of GAGs.

TABLE 4

| Test Sample | Formulation | GeoMean % RP |
|---|---|---|
| 1 | 154 mM sodium chloride, pH 6 | No effect |
| 2 | 154 mM sodium chloride supplemented with 0.005% (v/v) polysorbate 20, pH 6 | No effect |
| 3 | 20 mM sodium phosphate pH 6, with 137 mM sodium chloride and 0.02% (v/v) polysorbate 20 | No effect |
| Assay Positive Control | 66.4 mg/mL, 154 mM NaCl pH 6 | 101 |

Robustness

To assess the robustness of the assay of the present invention, a design of experiment (DOE) study was designed to examine the effect of variation of factors on the method. This study included variations of three different factors: cell number/well $^{35}$S radiolabelling incubation time, and dose treatment incubation time. In the study, maximum signal/minimum GAG clearance was assessed. Each run incorporated four plates, which tested assay control and samples for three potency levels of the assay positive control (41% RP, 100% RP and 243% RP) covering the linear range of the method. GeoMean, 95% CI, % GCV and % Relative Accuracy were determined. The observed % GCV values within the robustness assessment are consistent with the observed precision GCV of 10.3%. Additionally, the mean % relative accuracy is within 97.8-107%, which is consistent with the % relative accuracy measured from the dilutional linearity data. These data indicate that all of the conditions tested demonstrated no effect on the observed relative potency, hence the assay is robust and accurate.

Thus, the substrate clearance assay according to the present invention may be used to effectively characterize cellular uptake process.

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

What is claimed is:

1. A method of measuring enzymatic activity of a recombinant lysosomal enzyme, comprising steps of
    obtaining a sample from a manufacturing process comprising a recombinant lysosomal enzyme of interest;
    contacting the sample comprising the lysosomal enzyme of interest with cells containing a substrate of the lysosomal enzyme labeled with a radioactive isotope cleavable by the lysosomal enzyme, under conditions that allow the lysosomal enzyme to cleave the radioactive isotope from the substrate, wherein the cells are attached to a scintillant base such that scintillation events are indicative of radioactive emission level associated with the cells; measuring a change of radioactive emission level associated with the cells by detecting scintillation events as compared to baseline scintillation events before the contacting step, wherein a decrease in scintillation events after the contacting step relative to baseline scintillation is indicative of enzymatically active lysosomal enzyme; and
    measuring the enzymatic activity of the lysosomal enzyme based on the change of radioactive emission level associated with the cells as compared to a control, wherein the control is a reference standard indicative of a predetermined enzymatic activity of the lysosomal enzyme of interest,
    wherein the method does not involve lysis of the cells;
    thereby measuring enzymatic activity of a recombinant lysosomal enzyme.

2. The method of claim 1, wherein the cells lack endogenous lysosomal enzyme of interest.

3. The method of claim 1, wherein the cells are fibroblasts derived from patients suffering from a lysosomal storage disease associated with a deficiency of the lysosomal enzyme of interest.

4. The method of claim 1, wherein the substrate of the lysosomal enzyme labeled with the radioactive isotope is synthesized by the cells in the presence of the radioactive isotope.

5. The method of claim 1, wherein the method further comprises steps of:
    growing cells to a desired confluency;
    treating the cells with the radioactive isotope such that the radioactive isotope is incorporated into newly synthesized substrate of the lysosomal enzyme; and
    seeding the cells into a well with the scintillant base such that the cells attach to the scintillant base.

6. The method of claim 1, wherein the substrate is glycosamine glycan (GAG).

7. The method of claim 6, wherein the radioactive isotope is $^{35}S$.

8. The method of claim 7, wherein the substrate is labeled by treating the cells with $^{35}S$-sodium sulfate.

9. The method of claim 1, wherein the conditions that allow the lysosomal enzyme to cleave the radioactive isotope from the substrate comprises incubating the cells and the sample comprising the lysosomal enzyme at 37° C. with 5% $CO_2$ in atmosphere.

10. The method of claim 1, wherein the method further comprises a step of washing the cells prior to the measuring step.

11. The method of claim 1, wherein the contacting step is carried out in the presence of mannose-6-phosphate (M6P) and wherein the method further comprises a step of comparing the enzyme activity to a control measured without M6P to determine if cellular uptake is M6P dependent.

* * * * *

UNITED STATES PATENT AND TRADEMARK OFFICE
CERTIFICATE OF CORRECTION

| | | |
|---|---|---|
| PATENT NO. | : 11,187,697 B2 | |
| APPLICATION NO. | : 15/119324 | |
| DATED | : November 30, 2021 | |
| INVENTOR(S) | : Chhajlani | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Signed and Sealed this
Twentieth Day of December, 2022

Katherine Kelly Vidal
*Director of the United States Patent and Trademark Office*